(12) United States Patent
Okuno et al.

(10) Patent No.: US 6,380,399 B1
(45) Date of Patent: Apr. 30, 2002

(54) PROCESS FOR PRODUCING PHTHALIC ANHYDRIDE

(75) Inventors: Masaaki Okuno; Tsukasa Takahashi, both of Himeji (JP)

(73) Assignee: Nippon Shokubai Co., Ltd., Osaka-fu (JP)

( * ) Notice: Subject to any disclaimer, the term of this patent is extended or adjusted under 35 U.S.C. 154(b) by 0 days.

(21) Appl. No.: 09/602,007

(22) Filed: Jun. 23, 2000

(30) Foreign Application Priority Data

Jun. 24, 1999 (JP) .......................................... 11-178788

(51) Int. Cl.⁷ ............................................. C07D 307/89
(52) U.S. Cl. ....................................... 549/250; 549/251
(58) Field of Search ................................. 549/250, 251

(56) References Cited

U.S. PATENT DOCUMENTS

| | | |
|---|---|---|
| 3,843,552 A | 10/1974 | Jouy et al. |
| 3,909,457 A | 9/1975 | Friedrichsen et al. |
| 3,926,846 A | 12/1975 | Ono et al. |
| 4,046,780 A | 9/1977 | Nakanishi et al. |
| 4,077,984 A | 3/1978 | Blechschmitt et al. |
| 4,356,112 A | 10/1982 | Nakanishi et al. |
| 4,879,387 A | * 11/1989 | Hara |

FOREIGN PATENT DOCUMENTS

| | | |
|---|---|---|
| CA | 862736 | 2/1971 |
| DE | 2830765 | 1/1980 |
| EP | 0522871 | 1/1993 |
| EP | 0792866 | 9/1997 |
| JP | 57-105241 | 6/1982 |

OTHER PUBLICATIONS

Koichi et al., "Acrylic acid production", WPI World Patent Information Derwent, Derwent, GB, XP002146736.

* cited by examiner

*Primary Examiner*—T. A. Solola
(74) *Attorney, Agent, or Firm*—Wenderoth, Lind & Ponack, L.L.P.

(57) ABSTRACT

The invented process produces phthalic anhydride through gas-phase catalytic oxidation of ortho-xylene and/or naphthalene with an oxygen-containing gas using one or more fixed bed reactors. In the process, the gas-phase catalytic oxidation process is performed in three or more individual catalytic layers, and the conversion rates of ortho-xylene and/or naphthalene in the individual layers are controlled within specific ranges. The process is capable of providing phthalic anhydride in a high yield, is capable of minimizing deterioration of catalysts with time, and is capable of continuously stably producing phthalic anhydride in safety, even when a high concentration material gas is fed.

15 Claims, 5 Drawing Sheets

PROCESS FOR PRODUCING PHTHALIC ANHYDRIDE

BACKGROUND OF THE INVENTION

1. Field of the Invention

The present invention relates to a process for producing phthalic anhydride using a fixed bed reactor. Particularly, the invention relates to a process for producing phthalic anhydride in a high yield by gas-phase catalytic oxidation of ortho-xylene and/or naphthalene with molecular oxygen or an molecular-oxygen-containing gas using a fixed bed reactor.

2. Description of the Related Art

Phthalic anhydride is produced by a process of gas-phase catalytic oxidation of ortho-xylene and/or naphthalene with molecular oxygen or a molecular-oxygen-containing gas (these are hereinafter briefly referred to as "oxygen-containing gas"). In this process, the use of catalysts each containing vanadium oxide and titanium oxide as active ingredients supported on an inert carrier is widely known, and is described in, for example, Japanese Examined Patent Application Publications No. 47-15323, No. 49-41036, and No. 52-4538, and Japanese Unexamined Patent Application Publications No. 47-5661, No. 49-89694, and No. 57-105241. These catalysts each have a feature and some of them have been used in commercial production.

However, the performances of such catalysts are susceptible to improvement. In consideration of the scale of production system, even a 1% increase in yield of phthalic anhydride by an improvement of a catalyst can give large economic effects. An improvement in selectivity can facilitate heat treatment and distillation procedure to yield a final product and is thereby expected to produce high quality products at low costs.

In addition, it is important to ensure a stable production through an increased productivity and a durable catalytic activity. A possible solution to increase the productivity is to conduct an oxidation reaction under high loading conditions. For example, the concentration of a raw material gas (ortho-xylene and/or naphthalene) relative to an oxygen-containing gas is to be increased. However, a reaction of ortho-xylene and/or naphthalene to yield phthalic anhydride is a highly exothermic reaction, and under such high loading conditions, the temperature of a hot spot vigorously increases and an excessive oxidation reaction occurs to markedly deteriorate the catalyst. As a result, the yield of phthalic anhydride is decreased. If the temperature of the hot spot excessively increases, heat of reaction cannot be sufficiently removed, which will induce a runaway reaction.

Catalysts having a satisfactory heat resistance and stable toward the use under such high loading conditions have been proposed, for example in Japanese Examined Patent Application Publication No. 59-1378. However, even when such catalysts are used, decrease in the yield of phthalic anhydride, deterioration of catalyst and the danger of a runaway reaction cannot be avoided unless excessive temperature rise in a hot spot is controlled.

Under these circumstances, to performed operations under high loading conditions, an attempt has been made to inhibit the temperature rise in the hot spot by configuring the catalytic layer as two or more individual catalytic layers having different catalytic activities. However, if conversion of a raw material in individual catalytic layers is out of valance, the temperature in a hot spot still excessively vigorously rises to thereby invite an excessive oxidation reaction. As a result, this configuration cannot also solve the problems of decrease in yield of phthalic anhydride and deterioration of the catalyst. In extreme cases, a runaway reaction in the hot spot will occur.

SUMMARY OF THE INVENTION

Accordingly, an object of the invention is to provide a process for producing phthalic anhydride, which is capable of providing phthalic anhydride in a high yield, is capable of minimizing deterioration of catalysts with time, and is capable of continuously stably producing phthalic anhydride, even when a high concentration raw material gas is fed.

Specifically, the invention provide a process for producing phthalic anhydride through gas-phase catalytic oxidation of ortho-xylene and/or naphthalene with an oxygen-containing gas using one or more fixed bed reactors. In the process, the gas-phase catalytic oxidation process is performed in three or more individual catalytic layers, and the conversion rates of ortho-xylene and/or naphthalene in the individual catalytic layer are defined within specific ranges.

BRIEF DESCRIPTION OF THE DRAWINGS

Each of FIGS. 1 to 4 is a diagram showing an embodiment of production system for use in the invented production process where the catalytic layer is composed of three individual catalytic layers.

DESCRIPTION OF THE PREFERRED EMBODIMENT

The present inventors found that an excessive temperature rise of a hot spot in each individual catalytic layer can be suppressed by configuring the catalytic layer for the catalytic oxidation process as three or more individual catalytic layers and by specifying conversion rates in the individual catalytic layers to thereby balance the reaction amounts of the individual catalytic layers. The invention has been accomplished based on these findings.

Specifically, the invented process in an aspect produces phthalic anhydride through gas-phase catalytic oxidation of ortho-xylene and/or naphthalene with an oxygen-containing gas using one or more fixed bed reactors. In the process, the gas-phase catalytic reaction is performed in three or more individual catalytic layers, the conversion rate from ortho-xylene and/or naphthalene at an outlet of a first catalytic layer is 30% to 70%, and the conversion rate from ortho-xylene and/or naphthalene at an outlet of a second catalytic layer is 70% or more.

Preferably, the gas-phase catalytic reaction is performed in three individual catalytic layers, and the conversion rate from ortho-xylene and/or naphthalene at an outlet of a first catalytic layer is 30% to 70%, the conversion rate from ortho-xylene and/or naphthalene at an outlet of a second catalytic layer is 70% to 95%, and the conversion rate from ortho-xylene and/or naphthalene at an outlet of a third catalytic layer is 99% or more.

The above conversion rates can be achieved by sequentially increasing the activity of each catalyst constituting each individual catalytic layer in the order from the first catalytic layer to the second catalytic layer, and to the third catalytic layer.

The term "conversion rate" as used herein means a rate of the conversion of ortho-xylene and/or naphthalene for use as a raw material for phthalic anhydride, and compounds produced by conversion include not only a final product phthalic anhydride but also compounds formed during the course of the production of phthalic anhydride, such as ortho-tolualdehyde, phthalide, maleic anhydride, citraconic anhydride, benzoic acid, carbon monoxide, and carbon dioxide.

In the invention, the conversion rate is measured in the following manner.

Catalytic layers from the first catalytic layer to a catalytic layer to be measured are formed, and layers corresponding to subsequent catalytic layers are packed with an inert substance. For example, to determine the conversion rate in the first catalytic layer, the first catalytic layer is formed and layers corresponding to the second and subsequent catalytic layers are packed with an inert substance having no catalytic activity, and then the conversion rate is determined. To determine the conversion rate of the second catalytic layer, the first and second catalytic layers are formed successively, and layers corresponding to the third and subsequent catalytic layers are packed with an inert substance. Under these conditions, a raw material gas (ortho-xylene and/or naphthalene) and an oxygen-containing gas are introduced into the reactor under an actual operation condition, and a gas from the outlet of the reactor is collected. The collected outlet gas is dissolved in acetone, and the resulting acetone solution is analyzed by gas chromatography to determine the amount of unreacted raw material gas. The conversion rate is calculated according to the following equation:

Conversion rate (%)=[1−(u/i)]×100 wherein "u" is the amount (gram) of the raw material gas contained in the collected outlet gas, and "i" is the amount (gram) of a fed raw material gas corresponding to the amount of the collected outlet gas.

The conversion rate at an outlet of the first catalytic layer is specified in a range from 30% to 70%. If the conversion rate is less than 30%, a gas containing excessively large amounts of the raw material is introduced into the second catalytic layer, and loads on the second catalytic layer are increased. As a result, the hot spot temperature in the second catalytic layer excessively increases to thereby deteriorate the yield of phthalic anhydride.

In contrast, if the conversion rate at an outlet of the first catalytic layer exceeds 70%, the hot spot temperature in the first catalytic layer extremely increases as excessively large amounts of heat is evolved in the first catalytic layer, and the reaction in the first catalytic layer becomes markedly unstable. In this case, the hot spot cannot be significantly controlled to invite a runaway reaction. Even if no runaway reaction occurs, the catalyst is thermally deteriorated in the hot spot, and the yield of phthalic anhydride is further deteriorated with time.

The conversion rate at an outlet of the second catalytic layer is specified at 70% or more. If the conversion rate is less than 70%, loads on the third and subsequent layers are increased, and the hot spot temperature in each of the third and subsequent layers rises to thereby deteriorate the yield of phthalic anhydride. In addition, the reaction cannot be completed in catalytic layers from the third catalytic layer to a final catalytic layer, and the quality of product phthalic anhydride cannot be maintained.

Each of the individual catalytic layers is prepared in practice in the following manner. By taking a system comprising three individual catalytic layers as example, several embodiments of the invention will be illustrated with reference to FIGS. 1 to 4.

Figure 1:
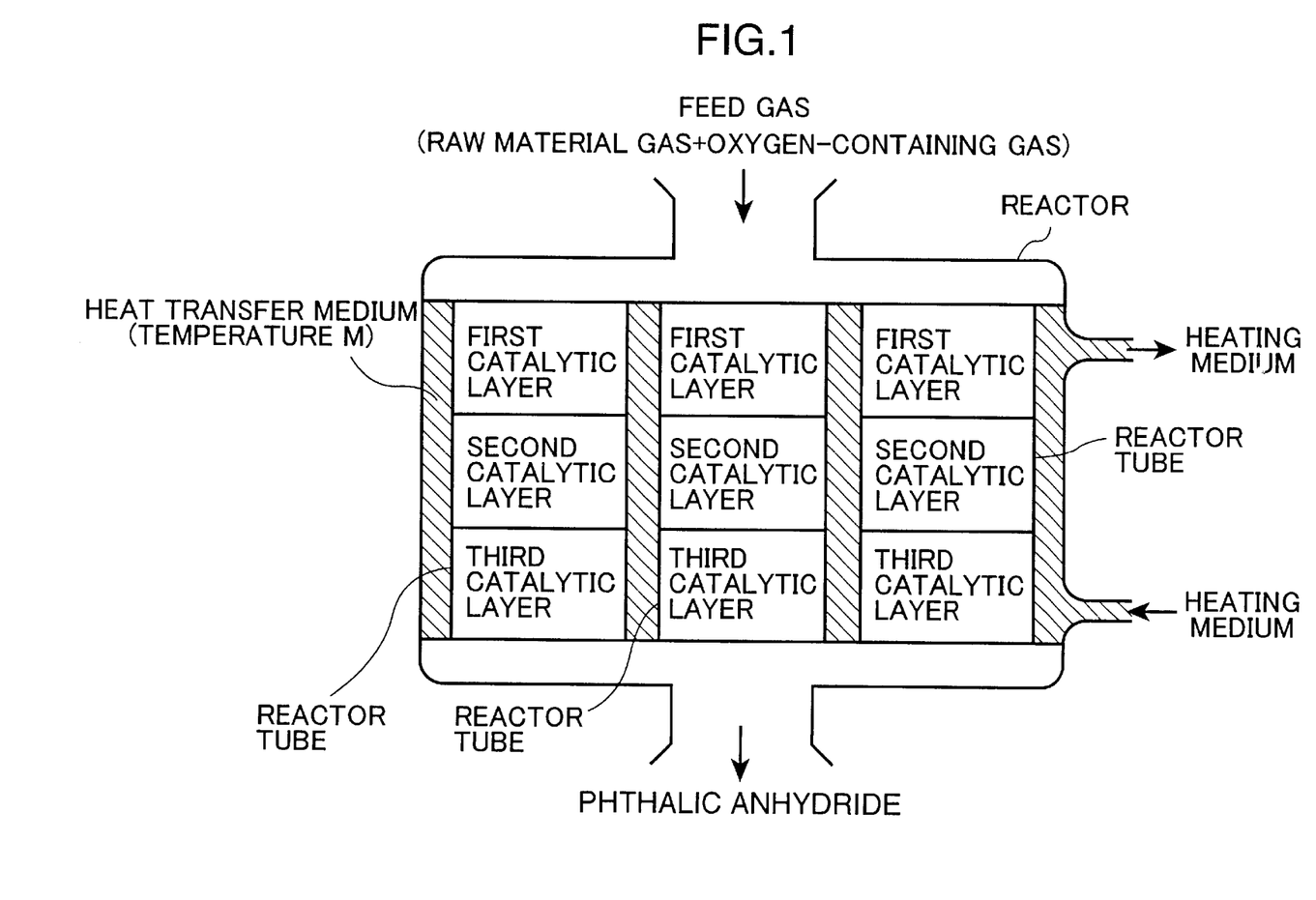
FIG. 1 is a diagram showing a system including a first catalytic layer, a second catalytic layer, and a third catalytic layer stacked in this order from an inlet of a single reactor.

In a first embodiment as shown in FIG. 1, a system is composed of a single reactor including first, second and third catalytic layers stacked in this order from the gas inlet side (continuous catalytic layer type). The reactor for use in this system is a multitubular fixed bed reactor. Each reactor tube includes the first, second, and third catalytic layers stacked in this order. FIG. 1 illustrates an example where the raw material gas and the oxygen-containing gas are fed from the top of the reactor, and the product phthalic anhydride is drawn from the bottom. The present embodiment is not limited to this example, and the system can be also configured as feeding gases from the bottom of the reactor and drawing phthalic anhydride from the top.

Figure 2:
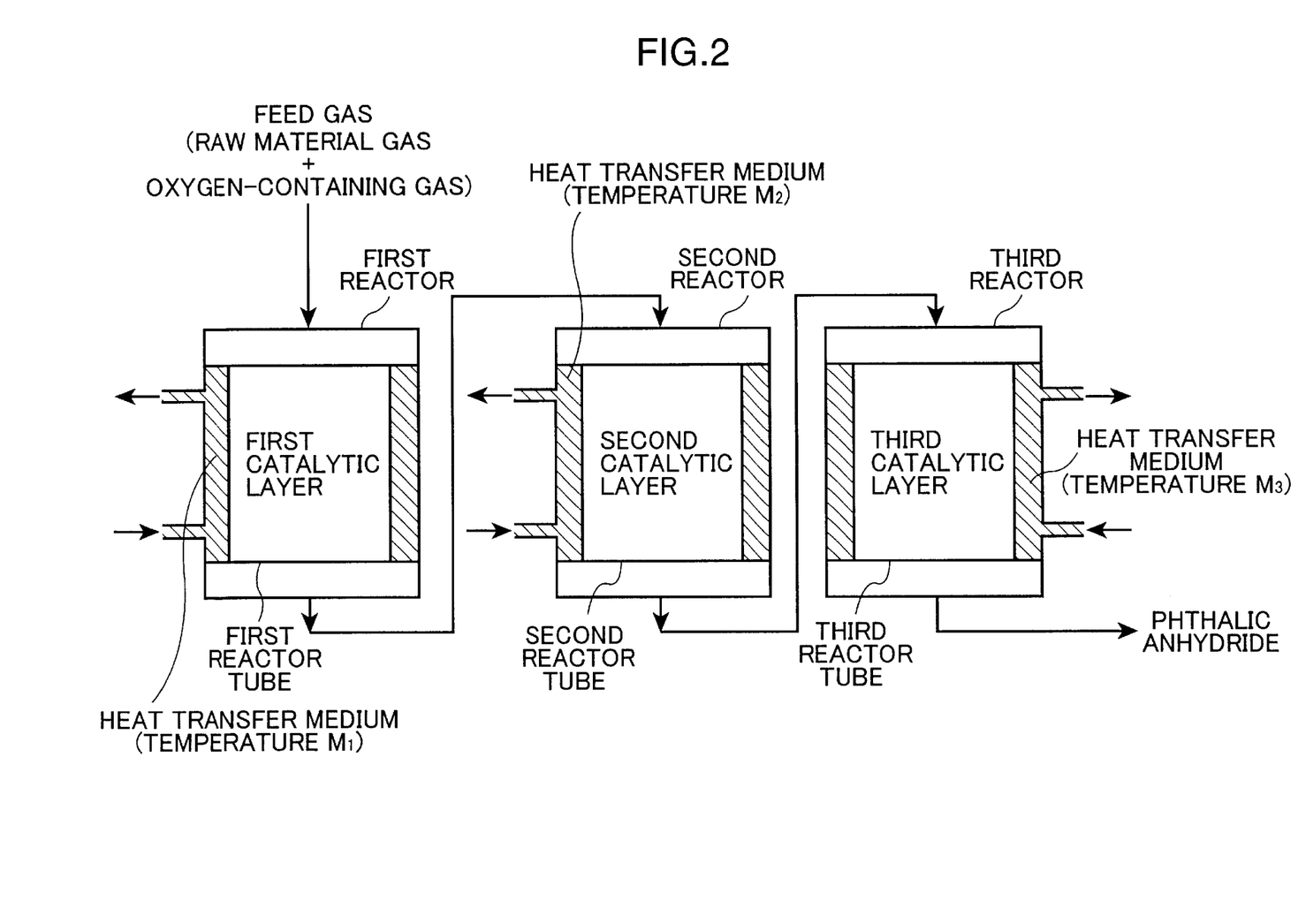
FIG. 2 is a diagram showing an embodiment using plural reactors connected in series, in which all the first, second, and third catalytic layers are formed in each of the first, second, and third reactors. Each of FIGS. 3 and 4 is a diagram showing an embodiment using two reactors connected in series, where two catalytic layers are stacked and formed in either one of the two reactors.

In a second embodiment as shown in FIG. 2, a system is composed of plural reactors which are connected in series and each contains one catalytic layer formed therein (discontinuous catalytic layer type). In this embodiment, the system includes a first reactor with a first catalytic layer, a second reactor with a second catalytic layer, and a third reactor with a third catalytic layer in the order from the gas supply side. In the system shown in FIG. 2, gases are fed from the top of each of the reactors, but the present embodiment is not limited to this configuration and the gases may be fed from the bottom by reversing the order of the catalytic layers. Each of the reactors includes a single tubular reactor in this example, but a multitubular fixed bed reactor as in the reactor used in the system shown in FIG. 1 can also be employed to increase the yield in commercial production.

Figure 3:
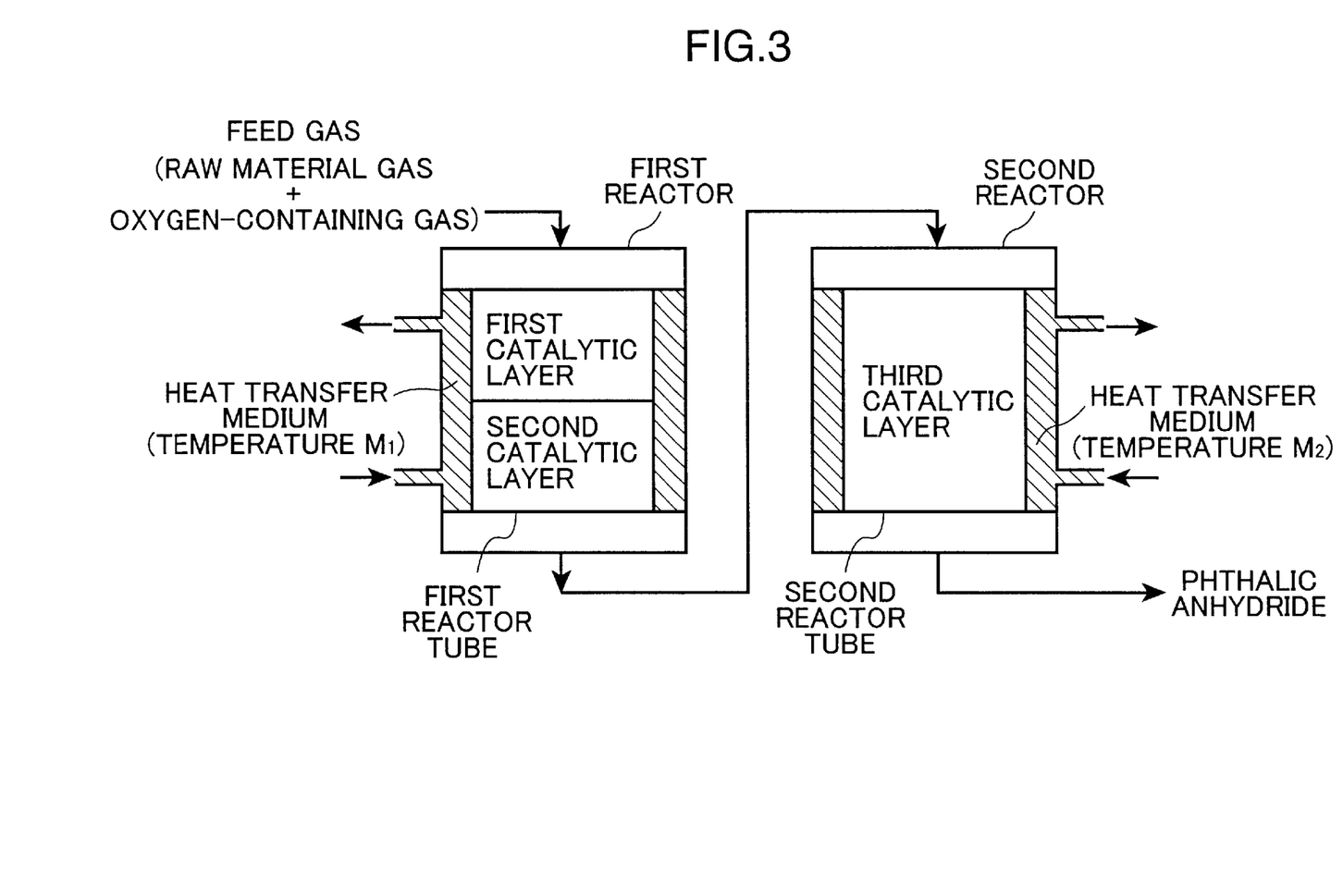
Figure 4:
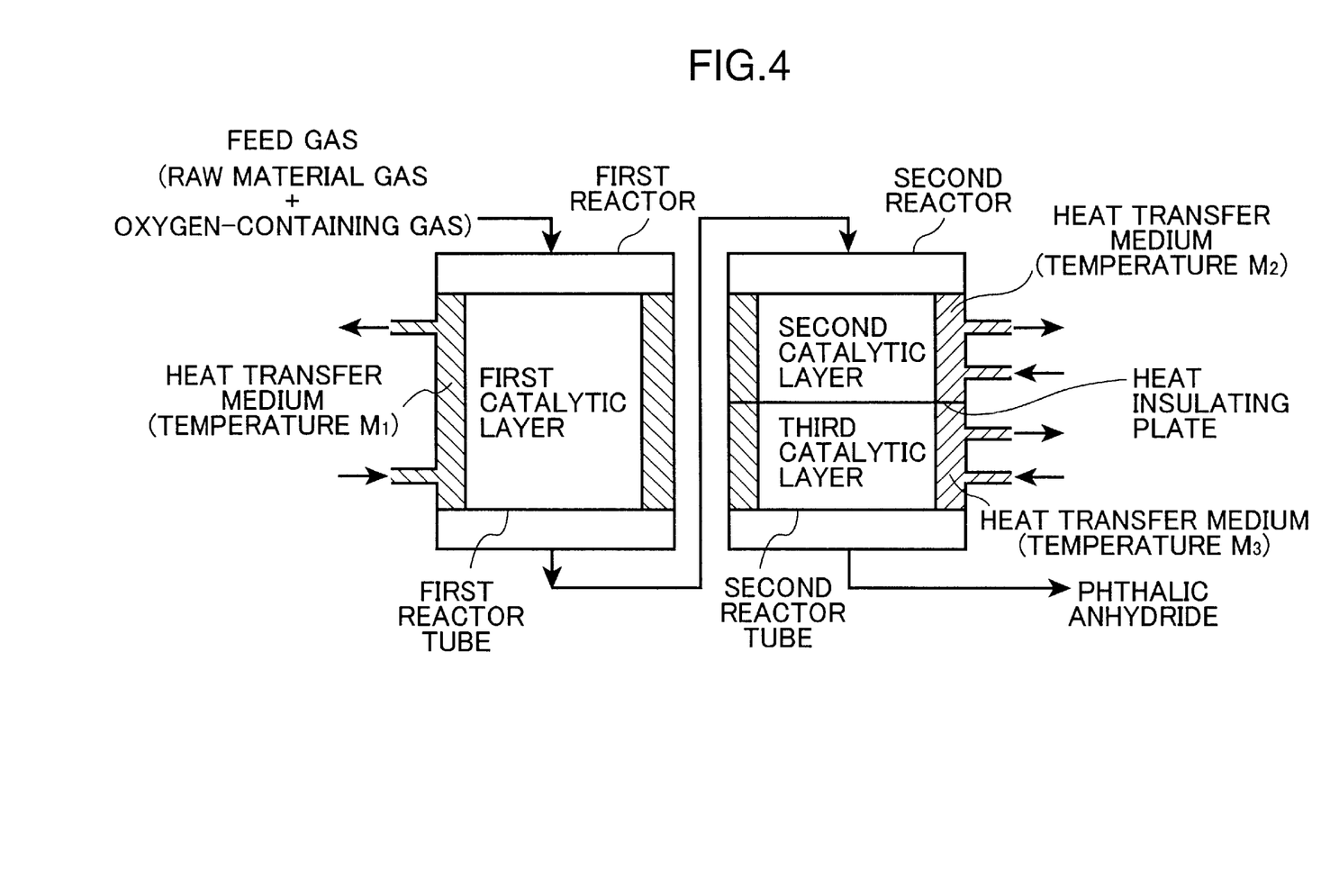

In a third embodiment as shown in FIGS. 3 and 4, a system is composed of a combination of a continuous catalytic layer type system and a discontinuous catalytic layer type system. In a system shown in FIG. 3, a reactor (a first reactor) arranged on the inlet side includes first and second catalytic layers stacked, and a reactor (a second reactor) arranged on the outlet side includes a third catalytic layer. In a system shown in FIG. 4, a reactor (a first reactor) arranged on the inlet side includes the first catalytic layer, and a reactor (a second reactor) arranged on the outlet side includes the second and third catalytic layers stacked in order.

In reactors for use in the invention, the temperatures of the catalytic layers are held at constant levels by circulating heat transfer media held at constant temperatures around reactor tubes filled with the catalysts. Accordingly, in the embodiment shown in FIG. 2, each temperature of each individual catalytic layer can be independently set at a constant level by changing the temperature of each heat transfer medium circulated around each reactor. Even in a continuous catalytic layer type system, each of the temperatures at which individual catalytic layers held can be independently changed by separating the reactor with a heat insulating plate, and circulating each of heating media having different temperatures around each individual catalytic layer, as in the second reactor shown in FIG. 4.

The term "individual catalytic layer" as used herein means an area in which an oxidation process showing an independent individual hot spot temperature is performed. Specifically, when catalysts having the identical composition are used but different hot spot temperatures are observed, for example, when the reactors in the system shown in FIG. 2 are to have different catalytic activities from one another by changing the temperatures of the heat transfer media in individual reactors, the system is considered to be composed of a series of independent individual catalytic layers. In contrast, when even two types of catalysts are stacked to form a two-layer catalytic system but only a single hot spot temperature is observed, the two-layer catalytic layer is considered as a single catalytic layer.

Figure 5:
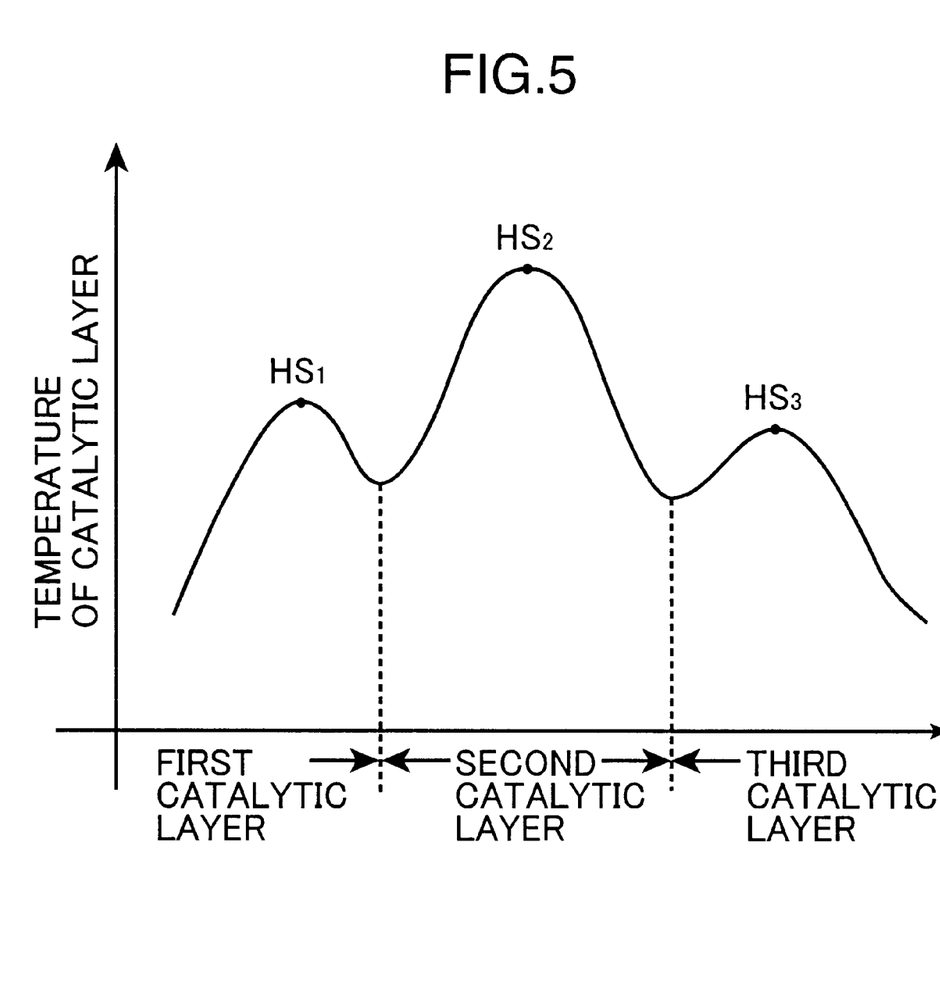
FIG. 5 is a graph showing temperature changes in the catalytic layers in the invented production process, wherein $HS_1$, $HS_2$, and $HS_3$ are respectively the hot spot temperatures in the first, second, and third catalytic layers.

The term "hot spot temperature" as used herein means the maximum temperature in the catalytic layer in question. Specifically, the hot spot temperature is the maximum temperature obtained by measuring temperatures at different positions of the catalytic layer during reaction. Accordingly, when the system includes three individual catalytic layers and temperatures of the catalytic layers are determined in the invented process for producing phthalic anhydride, the results are illustrated as in the graph shown in FIG. 5. In FIG. 5, the individual catalytic layers show different peak temperatures (maximum temperatures), wherein $HS_1$ is the hot spot temperature in the first catalytic layer, $HS_2$ is the hot spot temperature in the second catalytic layer, and $HS_3$ is the hot spot temperature in the third catalytic layer.

According to the invention, $\Delta T$ as defined according to the following equation is preferably 0.35 to 0.85° C./(g/Nm$^3$) in the first catalytic layer, and is 0.45 to 1.20° C./(g/Nm$^3$) in the second catalytic layer. When the system includes three individual catalytic layers, $\Delta T$ is preferably 0.25 to 0.70° C./(g/Nm$^3$) in the third catalytic layer:

$$\Delta T=(HS-M)/W$$

wherein HS is the hot spot temperature (°C.) in each individual catalytic layer, M is the temperature (°C.) of each heat transfer medium for heating each individual catalytic layer, and W is the amount of the raw material gas (the total amount (g) of ortho-xylene and naphthalene) relative to 1 m$^3$ of the oxygen-containing gas at standard temperature and pressure.

In each individual catalytic layer, a $\Delta T$ exceeding the upper limit of the above range means that heat evolution in the catalytic layer in question excessively increases, and the conversion rates specified in the invention are hardly obtained. In contrast, a $\Delta T$ less than the lower limit of the above range means that the reaction amount in the catalytic layer in question excessively decreases. Loads on the other catalytic layers therefore increase and the reactions get out of balance to thereby deteriorate the yield of phthalic anhydride. In severe cases, heat evolution in the other catalytic layers excessively increase, and the conversion rates specified in the invention are hardly obtained.

The temperatures of the individual catalytic layers are usually determined with a multipoint thermocouple inserted in a direction along with the gas passage of the catalytic layer into the center of the cross section of the reactor tube. In this case, the temperatures of the catalytic layer should be determined using a reactor tube having such a diameter that the catalyst in the catalytic layer distributes uniformly even when the thermocouple is inserted, in consideration of the diameter of the thermocouple.

In the invented process, the catalytic activity of each individual catalytic layer should increase in the order from the first catalytic layer to the second and subsequent catalytic layers to achieve the conversion rate in each individual catalytic layer within the specified range.

In practice, the catalytic activity is sequentially increased by the following processes.

(1) A process for sequentially increasing the catalytic activity, in which a phosphorus-containing catalyst is used in each individual catalytic layer and the phosphorus content of the catalyst is sequentially increased in the order from the first catalytic layer to subsequent catalytic layers;

(2) a process for sequentially increasing the catalytic activity, in which each catalyst packed in each individual catalytic layer is supported on an inert carrier, and the supported catalyst is packed in such a manner that the supporting rate of the catalyst in each catalytic layer sequentially increases in the order from the first catalytic layer to subsequent catalytic layers;

(3) a process for sequentially increasing the catalytic activity, in which each catalyst packed in each individual catalytic layer is composed of at least one element selected from sodium, potassium, cesium, rubidium, and thallium, and the total content of the sodium, potassium, cesium, rubidium, and thallium in each individual catalytic layer sequentially decreases in the order from the first catalytic layer to subsequent catalytic layers;

(4) a process for sequentially increasing the catalytic activity, in which each catalyst packed in each individual catalytic layer is supported on an inert carrier, and the supported catalyst is packed in such a manner that the voidage in the reactor tube of each individual catalytic layer sequentially decreases in the order from the first catalytic layer to subsequent catalytic layers;

(5) a process for sequentially increasing the catalytic activity, in which each individual catalytic layer comprises a mixture of each catalyst and an inert substance, and the content of the inert substance in the mixture sequentially decreases in the order from the first catalytic layer to subsequent catalytic layers; and (6) a process for sequentially increasing the catalytic activity, in which the temperature of the heat transfer medium at which each individual catalytic layer is held sequentially increases in the order from the first catalytic layer to subsequent catalytic layers.

Each of these processes (1) to (6) can be employed alone or in combination. Particularly, the combination of the processes (3) and (4), and the combination of the processes (2) and (3) are preferred to change the catalytic activities within a wide range.

The term "voidage" of the catalytic layer as used in the process (4) means the ratio of a portion where the catalyst is not packed, i.e., the ratio of space, occupying the catalytic layer. The voidage can be changed by, for example, changing the size of a catalyst supported on an inert carrier to thereby change the packing ratio of the catalyst.

The process (6) can be applied to cases where each individual catalytic layer uses a different catalyst from one another or where each individual catalytic layer uses the identical catalyst to one another. To hold each individual catalytic layer at each independent temperature, a system including plural independent tubular reactors connected in series as shown in FIG. 2 may be used and the temperatures of heat transfer media circulating in the reactors may be set to be different. Alternatively, in a continuous catalytic layer type system, independent temperature control in each individual catalytic layer can be achieved by separating one reactor corresponding to the constituent catalytic layers and circulating each heat transfer medium held at a predetermined temperature in a portion corresponding to each individual catalytic layer.

Catalysts for use in the individual catalytic layers preferably comprise vanadium oxide and titanium oxide. More preferably, the catalysts further comprise niobium, phosphorus, and antimony, and particularly preferably further comprise at least one selected from the group consisting of sodium, potassium, rubidium, cesium, and thallium. In addition and advantageously, the catalysts comprise an anatase titanium dioxide having a specific surface area of 10 to 60 $m^2/g$ as the titanium oxide. Typically preferably, the catalysts are catalysts obtained by calcining a composition supported on an inert carrier at 500° C. to 600° C. under air flow for 2 to 10 hours, which composition is composed of vanadium oxide, an anatase titanium dioxide having a specific surface area of 10 to 60 $m^2/g$, niobium, phosphorus, antimony, and at least one selected from the group consisting of sodium, potassium, cesium, rubidium, and thallium. The catalytic activities of such catalysts can be easily changed by changing the supporting rate, by changing the content of sodium, potassium, cesium, rubidium, or thallium, or by changing the content of phosphorus.

Inert carriers for use in the invention must be stable at temperatures significantly higher than the temperature of calcining the catalyst and the temperature of the catalyst in the production of phthalic anhydride over a long time and must be inert to the catalytic substances. Such inert carriers include, but are not limited to, silicon carbide (SiC), steatite, cordierite, alumina, zirconium oxide, and titanium oxide. Of these carriers, a silicon carbide carrier having an alumina ($Al_2O_3$) content of 20% by weight or less, and preferably 5% by weight or less, and having an apparent porosity of 10% or more, and preferably 15% to 45% is advantageously employed. The more preferred carrier is a silicon carbide carrier obtained by self-sintering a powdered silicon carbide with a purity of 98% or more. The shape of the heat resistant inorganic inert carrier is not limited as far as the carrier has a mean particle size of about 2 to 15 mm, and preferably about 3 to 12 mm. Typically, the carrier may be spherical, pellet-like, cylindrical, or ring-form.

The catalytic component can be supported on the inert carrier by any process. Preferably, the catalytic component can be easily supported on the inert carrier by a process comprising the steps of placing a predetermined amount of the inert carrier into a rotary drum which can be heated from the outside, and spraying a liquid (slurry) containing the catalytic component onto the inert carrier while holding the temperature at 200° C. to 300° C. The supporting rate of the catalytic component relative to the inert carrier depends on the size and shape of the inert carrier used. When a spherical or cylindrical carrier is employed, the supporting rate is preferably 3 to 30 gram of the catalytic component to 100 ml of the inert carrier, and particularly preferably 5 to 20 gram of the catalytic component to 100 ml of the inert carrier.

The inert carrier can be also used as an inert substance for changing the catalytic activity of each individual catalytic layer. In this case, the catalytic activity of each individual catalytic layer can be sequentially increased by decreasing the content of the inert substance in the mixture used in each individual catalytic layer in the order from the first catalytic layer to subsequent catalytic layers.

The invented production process produces phthalic anhydride by introducing a raw material gas and an oxygen-containing gas into a fixed bed reactor having the catalytic layer and subjecting the reactants to gas-phase catalytic oxidation. By configuring the catalytic layer as three or more individual catalytic layers and sequentially increasing the catalytic activities in the order from the gas inlet side according to any of the aforementioned processes, the conversion rate of the raw material in each oxidation process of each individual catalytic layer can be controlled within the specified range.

As the raw material gas, ortho-xylene, naphthalene or a mixture of these compounds can be used. The oxygen-containing gas includes a pure oxygen gas or a diluted oxygen gas such as air.

When the catalytic layer is composed of three individual catalytic layers, the preferred production conditions of the invented process are as follows.

By using a reactor tube with an internal diameter of 15 to 40 mm, and preferably 15 to 27 mm, the catalyst is packed in the reactor to a total height of the first, second, and third catalytic layers of 1.5 to 4 m, and preferably 2 to 3.5 m. Preferably, the heights (or lengths) of the first, second, and third catalytic layers to the overall height of the catalytic layers are 25% to 54%, 21% to 54%, and 14% to 46%, respectively. The catalytic layers are preferably held at temperatures from 300° C. to 400° C., and more preferably from 330° C. to 380° C. The raw material gas is preferably fed into the reactor with an oxygen-containing gas having an oxygen content of 10% to 21% by volume, such as air. The concentration of the raw material gas relative to 1 m3 of the oxygen-containing gas at standard temperature and pressure should be preferably 70 gram (hereinafter indicated as "70 $g/Nm^3$") or more. Particularly, the raw material gas concentration is preferably 90 $g/Nm^3$ or more when ortho-xylene is used as the raw material, and, is preferably 75 $g/Nm^3$ or more when naphthalene is used as the raw material. The gas space velocity at standard temperature and pressure is preferably 1000 to 6000 $hr^{-1}$, and more preferably 1500 to 4000 $hr^{-1}$.

The conditions for the invented production process are not limited to the aforementioned conditions, and the configuration of the system used, the temperatures at which each individual catalytic layer is held, and the rate of the fed raw material gas can be selected within appropriate ranges, as far as the oxidation process of ortho-xylene and/or naphthalene is performed in three or more individual catalytic layers, and the conversion rates in the individual catalytic layers are within the specified ranges.

The invented production process is capable of suppressing temperature rise in a hot spot of each individual catalytic layer, is capable of minimizing deterioration of catalysts with time, and is capable of stably producing phthalic anhydride in a high yield, even when a high concentration material gas is fed.

EXAMPLE

The present invention will now be illustrated in more detail with reference to several invented examples and comparative examples below, which are not intended to limit the scope of the invention.

Measuring Method of Conversion Rate
A. Conversion Rate in Continuous Catalytic Layer Type System The conversion rate of the first catalytic layer was determined in the following manner.

Into an outlet side portion of an iron tubular reactor 25 mm in internal diameter and 3.5 m in length, a spherical SiC self-sintered carrier having a diameter of 6 mm, an apparent porosity of 35% and a purity of 98.5% by weight was packed to a height of 1.8 m corresponding to the heights of third and second catalytic layers. Onto the SiC self-sintered carrier layer, a first catalyst was packed to a height of 0.9 m to form a first catalytic layer.

Using a reactor composed of the above-prepared tubular reactor dipped in a molten salt bath, a gaseous mixture of a raw material gas and air was introduced into the reactor from an inlet under the conditions according to the production processes described below. The amount (u) of the raw material gas contained in a gas collected at the outlet was determined, and the amount (i) of the raw material gas corresponding to the volume of the gas collected at the outlet was estimated. The conversion rate from the material was calculated according to the following equation (1):

$$\text{Conversion rate from the material } (\%) = [1-(u/i)] \times 100 \quad (1)$$

wherein "u" is the amount (gram) of the raw material gas contained in the collected outlet gas, and "i" is the amount (gram) of a fed material gas corresponding to the raw amount of the collected outlet gas.

The conversion rate at the outlet of the second catalytic layer was determined in the following manner. Into an outlet side portion of the iron tubular reactor, the SiC self-sintered carrier was packed to a height of 0.9 m corresponding to the height of the third catalytic layer. Onto the SiC self-sintered carrier layer, a second catalyst was packed to a height of 0.9 m to form the second catalytic layer, and onto the second catalytic layer, a first catalyst was packed to a height of 0.9 m to form the first catalytic layer.

Using a reactor composed of the above-prepared tubular reactor dipped in a molten salt bath, a gaseous mixture of a raw material gas and air was introduced into the reactor from an inlet under the conditions according to the production processes described below, and the conversion rate was determined.

B. Conversion Rate in Discontinuous Catalytic Layer Type System

Three reactors were connected in series, and a first catalytic layer was formed in a first raw reactor arranged on the gas inlet side. A gaseous mixture of a raw material gas and air was introduced into the above-prepared first reactor under conditions according to the following production process, and the conversion rate of the raw material gas in the outlet gas of the first reactor was determined and was defined as the conversion rate of the first catalytic layer.

The conversion rate at the outlet of the second catalytic layer was determined as follows. The first and second catalytic layers were formed respectively in first and second reactors, which first reactor was arranged on the gas inlet side, and which second reactor was connected to the first reactor. A gaseous mixture of a material gas and air was introduced into the first reactor from the inlet under conditions according to the production processes described below, and the conversion rate of material gas in the outlet gas of the second reactor was determined and was defined as the conversion rate of the second catalytic layer.

Measuring Method of Hot Spot Temperature

A. Hot Spot Temperature in Continuous Catalytic Layer Type System

A multipoint thermocouple (12 measuring points) having diameter of 10 mm was inserted into an iron tubular reactor having internal diameter of 30 mm and length of 3.5 m. While holding the thermocouple at the center of the reactor tube, a third catalyst was packed to a height of 0.9 m into the outlet side portion of the reactor tube to form the third catalytic layer, subsequently, a second catalyst was packed thereon to a height of 0.9 m to form the second catalytic layer, and a first catalyst was then packed thereon to a height of 0.9 m to form the first catalytic layer. The temperatures of the above-prepared catalytic layers thus determined were almost identical to the temperatures of catalytic layers of the following production examples.

The temperature of a molten salt bath in which the tubular reactor was dipped was held at 350° C., and a gaseous mixture of a raw material gas and air was introduced into the reactor under conditions indicated in the following production examples to perform an oxidation reaction, and the temperatures of the catalytic layers were determined respectively at an initial stage of the reaction and 3 months after starting the reaction. The maximum temperature measured in the first catalytic layer was defined as the hot spot temperature ($HS_1$) of the first catalytic layer, the maximum temperature measured in the second catalytic layer was defined as the hot spot temperature ($HS_2$) of the second catalytic layer, and the maximum temperature measured in the third catalytic layer was defined as the hot spot temperature ($HS_3$) of the third catalytic layer.

B. Hot Spot Temperature in Discontinuous Catalytic Layer Type System

Three iron tubular reactors each having an internal diameter of 30 mm and a length of 1.5 m were connected in series, and one each multipoint thermocouple (12 measuring points) having diameter of 10 mm was inserted into each of the tubular reactors. While holding the thermocouple at the center of the reactor tube, a catalytic layer 0.9 m high was formed in each reactor tube. The temperatures of molten salt baths in which the individual tubular reactors were dipped were controlled to predetermined ranges according to the production processes described below, and a gaseous mixture of a raw material gas and air was introduced into the tubular reactors. The temperatures of each individual catalytic layer during oxidation reaction were determined. The maximum temperature measured in the first tubular reactor was defined as the hot spot temperature ($HS_1$) of the first catalytic layer, the maximum temperature measured in the second tubular reactor was defined as the hot spot temperature ($HS_2$) of the second catalytic layer, and the maximum temperature measured in the third tubular reactor was defined as the hot spot temperature ($HS_3$) of the third catalytic layer.

Calculation of ΔT

The ΔT in each individual catalytic layer was calculated according to the following equation:

$$\Delta T = (HS - M)/W$$

wherein HS is the hot spot temperature (°C.) measured in each individual catalytic layer, M is the temperature (°C.) of a molten salt bath (heat transfer medium) in which each tubular reactor is dipped, and W is the total mass (g) of the material (ortho-xylene and/or naphthalene) relative to 1 m³ of air at standard temperature and pressure.

Preparation of Titanium Oxide

A titanium oxide for use as the catalytic component was prepared in the following manner.

A 80% concentrated sulfuric acid was added to ilmenite, and the resulting mixture was sufficiently reacted and was then diluted with water to yield a titanium sulfate aqueous solution. To this solution, a piece of iron as a reducing agent was added to reduce the iron in the ilmenite to a ferrous ion, and the resulting mixture was cooled, and ferrous sulfate was removed by precipitation to yield a titanium sulfate aqueous solution. Steam heated at 150° C. was blown into the titanium sulfate aqueous solution to precipitate hydrous titanium oxide. The precipitated hydrous titanium oxide was washed with water, was washed with an acid, and was then washed again with water. The washed hydrous titanium oxide was calcined at 800° C. in air flow for 4 hours. The sintered product was pulverized with jet stream to yield an anatase titanium dioxide having a mean particle size of 0.5 µm and a specific surface area of 22 m$^2$/g.

Preparation of Catalyst

A series of slurries as the materials of Catalysts A to U were prepared in the following manner.

The slurries were obtained by changing the proportion of ammonium dihydrogenphosphate or cesium sulfate to the proportions indicated in Table 2 in the catalyst slurry 1 or 2 having the composition indicated in Table 1. Each of the slurries was obtained by preparing an oxalic acid aqueous solution, adding predetermined amounts of ammonium metavanadate, ammonium dihydrogenphosphate, niobium chloride, cesium sulfate, potassium sulfate, and antimony trioxide to the oxalic acid aqueous solution, stirring the resulting mixture, adding the titanium oxide to the mixture, and stirring the mixture with an emulsifier.

Separately, 2000 ml of a SiC self-sintered carrier was placed in a stainless steel rotary furnace 35 cm in diameter and 80 cm in length, and the carrier was heated at a temperature of 200° C. to 250° C. Onto the preheated carrier, the above-prepared slurry was sprayed while rotating the furnace to yield the catalytic substances supported on the carrier. The resulting supported catalyst was then calcined at 570° C. under air flow for 6 hours to yield Catalysts A to U.

Carriers for use in Catalysts A to U were sintered SiC spheres each having the diameter indicated in Table 2 and having an apparent porosity of 35% and a purity of 98.5%. The supporting rates of the catalysts are shown in Table 2.

TABLE 1

|  | Material slurry composition 1 | Material slurry composition 2 |
| --- | --- | --- |
| Deionized water | 6400 ml | 6400 ml |
| Oxalic acid | 250 g | 200 g |
| Ammonium metavanadate | 121.86 g | 96.48 g |
| Ammonium dihydrogenphosphate | variate | variate |
| Niobium chloride | 15.41 g | 15.25 g |
| Cesium sulfate | variate | variate |
| Potassium sulfate | 0.35 g | 0.69 g |
| Antimony trioxide | 37.89 g | 37.50 g |
| Titanium oxide | 1800 g | 1800 g |

TABLE 2

| Catalyst | Material slurry composition No. | Ammonium dihydrogen-phosphate (g) | Cesium sulfate (g) | Carrier diameter (mm) | Supporting rate (g/100 ml) |
| --- | --- | --- | --- | --- | --- |
| A | 1 | 3.07 | 12.17 | 6 | 8.0 |
| B | 1 | 9.21 | 12.17 | 6 | 8.0 |
| C | 1 | 24.57 | 12.17 | 6 | 8.0 |
| D | 1 | 9.21 | 12.17 | 6 | 5.0 |
| E | 1 | 9.21 | 12.17 | 6 | 12.0 |
| F | 1 | 9.21 | 15.57 | 6 | 8.0 |
| G | 1 | 9.21 | 5.35 | 6 | 8.0 |
| H | 1 | 9.21 | 12.17 | 9 | 7.0 |
| I | 1 | 9.21 | 12.17 | 4 | 9.0 |

TABLE 2-continued

| Catalyst | Material slurry composition No. | Ammonium dihydrogen-phosphate (g) | Cesium sulfate (g) | Carrier diameter (mm) | Supporting rate (g/100 ml) |
| --- | --- | --- | --- | --- | --- |
| J | 1 | 9.21 | 6.08 | 6 | 8.0 |
| K | 2 | 1.52 | 14.69 | 6 | 8.0 |
| L | 2 | 12.16 | 14.69 | 6 | 8.0 |
| M | 2 | 30.39 | 14.69 | 6 | 8.0 |
| N | 2 | 12.16 | 26.00 | 6 | 8.0 |
| O | 2 | 12.16 | 4.82 | 6 | 8.0 |
| P | 1 | 9.21 | 18.73 | 6 | 8.0 |
| Q | 1 | 9.21 | 13.87 | 6 | 8.0 |
| R | 1 | 6.14 | 12.17 | 6 | 8.0 |
| S | 2 | 12.16 | 29.37 | 6 | 8.0 |
| T | 2 | 6.08 | 14.69 | 6 | 8.0 |
| U | 2 | 12.16 | 18.78 | 6 | 8.0 |

Production of Phthalic Anhydride Through Ortho-xylene Oxidation

Production Example 1

Into an iron tubular reactor 25 mm in internal diameter and 3.5 m in length, Catalyst C as a third catalyst was packed to a height of 0.9 m to form the third catalytic layer, and onto this layer Catalyst B as a second catalyst was packed to a height of 0.9 m to form the second catalytic layer, and Catalyst A as a first catalyst was then packed thereonto to a height of 0.9 m to form the first catalytic layer.

The above-prepared tubular reactor was dipped into a molten salt bath at 350° C., and a mixed gas containing ortho-xylene and air in a ratio of 100 g/Nm$^3$ (100 gram of ortho-xylene relative to 1 m$^3$ of air at standard temperature and pressure) was fed into the dipped tubular reactor at a rate of 4.0 Nm$^3$/hr (space velocity at standard temperature and pressure: 3000 Hr$^{-1}$).

The yield of phthalic anhydride and the amount of phthalide, an intermediate by-product, were determined respectively at an initial stage of the reaction and 3 months after starting the reaction. The conversion rates of the first and second catalytic layers, and the hot spot temperatures of the first, second, and third catalytic layers under the above production condition were measured respectively at an initial stage of the reaction and 3 months after starting the reaction, according to the measuring methods in continuous catalytic layer type system. Tables 3 and 4 show the results at an initial stage of the reaction and the results 3 months after starting the reaction, respectively.

The conversion rate from ortho-xylene is nearly 100%, and the yield of phthalic anhydride can be regarded as the selectivity of phthalic anhydride.

Production Examples 2 to 4

Phthalic anhydride was produced in the same manner as in Production Example 1, except that the first, second, and third catalysts were changed to those indicated in Tables 3 and 4, and that the temperatures (M) of the molten salt baths were changed to those indicated in Tables 3 and 4. The conversion rates of the first and second catalytic layers, and the hot spot temperatures of the first, second, and third catalytic layers were measured respectively at an initial stage of the reaction and 3 months after starting the reaction, according to the measuring methods in continuous catalytic layer type system. In addition, the yield of phthalic anhydride and the amount of phthalide were determined. The results are shown in Table 3 (at an initial stage of the reaction) and Table 4 (3 months later).

Production Example 5

Each individual catalytic layer was formed from a mixture of Catalyst J and a spherical SiC self-sintered carrier having a diameter of 6mm, an apparent porosity of 35% and a purity of 98.5%. The contents of Catalyst J in the mixtures were set to 35% by weight, 60% by weight, and 100% by weight respectively for the first, second, and third catalytic layers.

Respectively at an initial stage of the reaction and 3 months after starting the reaction, the conversion rates of the first and second catalytic layers, and the hot spot temperatures of the first, second, and third catalytic layers were measured, according to the measuring methods in continuous catalytic layer type system. In addition, the yield of phthalic anhydride and the amount of phthalide were determined. The results are shown in Table 3 (at an initial stage of the reaction) and Table 4 (3 months later).

Production Example 6

Three iron tubular reactors each having an internal diameter of 25 mm and a length of 1.5 m were connected in series. Into each reactor, Catalyst B was packed to a height of 0.9 m to form the first, second, and third catalytic layers in the order from the gas inlet side.

The temperature ($M_1$) of a molten salt bath was held at 335° C. in which the tubular reactor (first tubular reactor) formed on the gas inlet side containing the first catalytic layer was dipped, and the temperature ($M_2$) of a molten salt bath was held at 350° C. in which the tubular reactor (second tubular reactor) containing the second catalytic layer was dipped, and the temperature ($M_3$) of a molten salt bath was held at 370° C. in which the tubular reactor (third tubular reactor) containing the third catalytic layer was dipped.

Under the same condition as in Production Example 1, a gaseous mixture of a material gas and air was then fed to the inlet of the first tubular reactor to perform an oxidation reaction. The conversion rates of the first and second catalytic layers, and the hot spot temperatures of the first, second, and third catalytic layers were measured respectively at an initial stage of the reaction and 3 months after starting the reaction, according to the measuring methods in discontinuous catalytic layer type system. In addition, the yield of phthalic anhydride and the amount of phthalide were determined. The results are shown in Table 3 (at an inital stage of the reaction) and Table 4 (3 months later).

TABLE 3

Raw material gas : ortho-xylene (100 g/Nm³)
Measured at an early stage of the reaction

| | Catalytic layer | | | Bath temperature | Conversion rate (%) | | upper line:HS (° C.) lower line:Δ t (° C.) | | | ΔT = Δ t/W | | | Yield Phthalic anhydride | Phthalide |
|---|---|---|---|---|---|---|---|---|---|---|---|---|---|---|
| No | 1st | 2nd | 3rd | M (° C.) | 1st | 2nd | 1st | 2nd | 3rd | 1st | 2nd | 3rd | (wt %) | (mol %) |
| 1 | A | B | C | 354 | 47 | 88 | 409 55 | 440 86 | 395 41 | 0.59 | 0.90 | 0.45 | 114.3 | 0.07 |
| 2 | D | B | E | 348 | 35 | 82 | 390 42 | 426 78 | 396 48 | 0.42 | 0.78 | 0.48 | 112.6 | 0.07 |
| 3 | F | B | G | 353 | 42 | 90 | 403 50 | 438 85 | 394 41 | 0.50 | 0.85 | 0.41 | 114.8 | 0.08 |
| 4 | H | B | I | 356 | 60 | 85 | 427 71 | 435 79 | 401 45 | 0.71 | 0.79 | 0.45 | 112.7 | 0.08 |
| 5 | J | J | J | 359 | 50 | 86 | 418 59 | 444 85 | 400 41 | 0.59 | 0.85 | 0.41 | 113.1 | 0.08 |
| 6 | B | B | B | 335 ($M_1$) 350 ($M_2$) 370 ($M_3$) | 45 | 89 | 387 52 | 437 87 | 410 40 | 0.52 | 0.87 | 0.40 | 113.5 | 0.08 |
| 7 | P | B | G | 353 | 25 | 93 | 376 23 | 510 157 | 368 15 | 0.23 | 1.57 | 0.15 | 108.5 | 0.04 |
| 8 | Q | B | G | 355 | 74 | 92 | 445 90 | 404 49 | 386 31 | 0.90 | 0.49 | 0.31 | 113.1 | 0.08 |
| 9 | A | R | C | 354 | 46 | 64 | 409 55 | 403 49 | 441 87 | 0.55 | 0.49 | 0.87 | 110.7 | 0.09 |

Δ t = HS − M

TABLE 4

Raw material gas : ortho-xylene (100 g/Nm³)
Measured 3 months later

| | Catalytic layer | | | Bath temperature | Conversion rate (%) | | upper line:HS (° C.) lower line:Δ t (° C.) | | | ΔT = Δ t/W | | | Yield Phthalic anhydride | Phthalide |
|---|---|---|---|---|---|---|---|---|---|---|---|---|---|---|
| No | 1st | 2nd | 3rd | M (° C.) | 1st | 2nd | 1st | 2nd | 3rd | 1st | 2nd | 3rd | (wt %) | (mol %) |
| 1 | A | B | C | 352 | 46 | 88 | 408 56 | 441 89 | 392 40 | 0.56 | 0.89 | 0.40 | 114.5 | 0.07 |

TABLE 4-continued

Raw material gas : ortho-xylene (100 g/Nm³)
Measured 3 months later

| | Catalytic layer | | | Bath temperature | Conversion rate (%) | | upper line:HS (° C.) lower line:Δ t (° C.) | | | Δ T = Δ t/W | | | Yield Phthalic anhydride | Phthalide |
|---|---|---|---|---|---|---|---|---|---|---|---|---|---|---|
| No | 1st | 2nd | 3rd | M (° C.) | 1st | 2nd | 1st | 2nd | 3rd | 1st | 2nd | 3rd | (wt %) | (mol %) |
| 2 | D | B | E | 347 | 35 | 84 | 389 42 | 427 80 | 395 48 | 0.42 | 0.80 | 0.48 | 112.6 | 0.07 |
| 3 | F | B | G | 350 | 45 | 91 | 402 52 | 438 88 | 388 38 | 0.52 | 0.88 | 0.38 | 115.3 | 0.07 |
| 4 | H | B | I | 356 | 64 | 89 | 433 77 | 432 76 | 400 44 | 0.77 | 0.76 | 0.44 | 112.5 | 0.07 |
| 5 | J | J | J | 358 | 55 | 88 | 422 64 | 445 87 | 399 41 | 0.64 | 0.87 | 0.41 | 112.9 | 0.06 |
| 6 | B | B | B | 335 (M₁) 348 (M₂) 370 (M₃) | 47 | 89 | 390 | 435 55 | 409 87 | 0.55 39 | 0.87 | 0.39 | 113.6 | 0.07 |
| 7 | P | B | G | 353 | 26 | 88 | 376 23 | 480 127 | 370 17 | 0.23 | 1.27 | 0.17 | 107.2 | 0.06 |
| 8 | Q | B | G | run away after 6 days from the starting the reaction | | | | | | | | | | |
| 9 | A | R | C | 353 | 48 | 66 | 410 57 | 403 50 | 440 87 | 0.57 | 0.50 | 0.87 | 110.5 | 0.09 |

Δ t = HS −M

Of the above production examples, Production Examples 1 to 6 are invented examples, and Production Examples 7 to 9 are comparative examples.

Tables 3 and 4 show that when the conversion rate in the first catalytic layer was low (Production Example 7), the yield of phthalic anhydride was lower than the other examples. In contrast, when the conversion rate in the first catalytic layer was excessively high (Production Example 8), the reaction ran away after 6 days from starting the reaction. When the conversion rate in the first catalytic layer was appropriate but the conversion rate in the second catalytic layer was low (Production Example 9), the yield of phthalic anhydride was lower than, and the formation of by-produced phthalide was higher than those in the invented examples (Production Examples 1 to 6).

In contrast, Production Examples 1 to 6 corresponding to the invented examples showed equivalent conversion rates and hot spot temperatures in each individual catalytic layer even after 3 months from starting the reaction to those at an initial stage of the reaction, indicating that stable reactions proceeded. The yields of phthalic anhydride were high.

Production of Phthalic Anhydride Through Naphthalene Oxidation

Production Example 10

Into an iron tubular reactor 25 mm in internal diameter and 3.5 m in length, Catalyst M as a third catalyst was packed to a height of 0.9 m to form the third catalytic layer, and onto this layer Catalyst L as a second catalyst was packed to a height of 0.9 m to form the second catalytic layer, and Catalyst K as a first catalyst was then packed thereonto to a height of 0.9 m to form the first catalytic layer.

The above-prepared tubular reactor was dipped into a molten salt bath at 365° C., and a gaseous mixture containing 90 g/Nm³ of naphthalene and air was fed into the dipped tubular reactor at a rate of 4.0 Nm³/hr (space velocity at standard temperature and pressure: 2900 Hr⁻¹).

The yield of phthalic anhydride and the amount of naphthoquinone, an intermediate by-product, were determined respectively at an initial stage of the reaction and 3 months after starting the reaction. The results are shown in Table 5. In this connection, the conversion rate from naphthalene was nearly 100%, and the yield of phthalic anhydride can be regarded as the selectivity of phthalic anhydride.

The conversion rates of the first and second catalytic layers, and the hot spot temperatures of the first, second, and third catalytic layers under the above production conditions were measured respectively at an initial stage of the reaction and 3 months after starting the reaction, according to the measuring methods in continuous catalytic layer type system. The results are set forth in Table 5.

Production Examples 11 to 14

Phthalic anhydride was prepared through an oxidation reaction of naphthalene in the same manner as in Production Example 10, except that the catalysts and the temperatures (M) of the molten salt baths of the individual catalytic layers were changed to those indicated in Table 5. Respectively at an initial stage of the reaction and 3 months after starting the reaction, the yield of phthalic anhydride and the amount of naphthoquinone were determined. The conversion rates of the first and second catalytic layers, and the hot spot temperatures of the first, second, and third catalytic layers under the above production conditions were measured, according to the measuring methods in continuous catalytic layer type system. The results are set forth in Table 5.

TABLE 5

Raw material gas: naphtalene (90 g/Nm³)

| production example | Catalytic layer | | | Bath temperature M (° C.) | Conversion rate (%) | | upper line:HS (° C.) lower line:Δ t (° C.) | | | ΔT = Δ t/W | | | Yield Phthalic anhydride (wt %) | Naphtho quinone (mol %) |
|---|---|---|---|---|---|---|---|---|---|---|---|---|---|---|
| | 1st | 2nd | 3rd | | 1st | 2nd | 1st | 2nd | 3rd | 1st | 2nd | 3rd | | |
| Measured at Initial stage | | | | | | | | | | | | | | |
| 10 | K | L | M | 365 | 55 | 83 | 435 / 70 | 433 / 68 | 395 / 30 | 0.78 | 0.76 | 0.33 | 104.2 | 0.40 |
| 11 | N | L | O | 360 | 49 | 85 | 423 / 63 | 440 / 80 | 391 / 31 | 0.70 | 0.89 | 0.34 | 104.6 | 0.39 |
| 12 | S | L | O | 365 | 24 | 87 | 390 / 25 | 502 / 137 | 379 / 14 | 0.28 | 1.52 | 0.16 | 98.3 | 0.26 |
| 13 | T | L | M | 368 | 78 | 94 | 479 / 111 | 410 / 42 | 378 / 10 | 1.23 | 0.47 | 0.11 | 101.1 | 0.41 |
| 14 | N | U | O | 360 | 49 | 63 | 425 / 65 | 393 / 33 | 438 / 78 | 0.72 | 0.37 | 0.87 | 98.6 | 0.60 |
| Measured at 3 months later | | | | | | | | | | | | | | |
| 10 | K | L | M | 360 | 55 | 85 | 432 / 72 | 435 / 75 | 392 / 32 | 0.80 | 0.83 | 0.36 | 104.0 | 0.38 |
| 11 | N | L | O | 360 | 51 | 88 | 425 / 65 | 442 / 82 | 390 / 30 | 0.72 | 0.91 | 0.33 | 105.0 | 0.36 |
| 12 | S | L | O | 365 | 25 | 80 | 391 / 26 | 478 / 113 | 384 / 19 | 0.29 | 1.26 | 0.21 | 96.4 | 0.31 |
| 13 | T | L | M | 373 | 73 | 93 | 466 / 98 | 421 / 53 | 385 / 17 | 1.09 | 0.59 | 0.19 | 98.2 | 0.40 |
| 14 | N | U | O | 360 | 51 | 65 | 427 / 67 | 396 / 36 | 436 / 76 | 0.74 | 0.40 | 0.84 | 99.2 | 0.57 |

Production Examples 10 and 11 corresponding to the invented examples showed stable conversion rates from naphthalene and stable hot spot temperatures from an initial stage of the reaction until 3 months into the reaction, and maintained a high yield of phthalic anhydride even after 3 months from starting the reaction.

In contrast, Production Example 12, where the conversion rate in the first catalytic layer was low, showed an excessively high hot spot temperature in the second catalytic layer and showed a low yield of phthalic anhydride from an initial stage of the reaction. Contrary to this, Production Example 13, where the conversion rate in the first catalytic layer was excessively high, exhibited an excessively high hot spot temperature in the first catalytic layer and invited a decrease in a yield of phthalic anhydride by about 3% after 3 months from starting the reaction. When the conversion rate in the first catalytic layer was in the specified range according to the invention but the conversion rate in the second catalytic layer was excessively low as in Production Example 14, the hot spot temperature in the third catalytic layer was excessively high and the overall yield of phthalic anhydride was low and the amount of by-produced naphthoquinone was increased.

Other embodiments and variations will be obvious to those skilled in the art, and this invention is not to be limited to the specific matters stated above.

What is claimed is:

1. A process for producing phthalic anhydride through gas-phase catalytic oxidation of ortho-xylene, or naphthalene, or both with an oxygen-containing gas using one or more fixed bed reactors, wherein said gas-phase catalytic reaction is performed in three or more individual catalytic layers, wherein each catalyst for use in each individual catalytic layer comprises vanadium oxide and titanium oxide;

the conversion rate from ortho-xylene, or naphthalene, or both at an outlet of a first catalytic layer is 30% to 70%; and the conversion rate from ortho-xylene, or naphthalene, or both at an outlet of a second catalytic layer is 70% or more.

2. A process according to claim 1, wherein ΔT as defined according to the following equation is 0.35 to 0.85° C./(g/Nm³) in the first catalytic layer, and is 0.45 to 1.20° C./(g/Nm³) in the second catalytic layer:

$$\Delta T = (HS - M)/W$$

wherein HS is the hot spot temperature (°C.) in each individual catalytic layer, M is the temperature (°C.) at which each individual catalytic layer is held, and W is the total amount (g) of ortho-xylene and naphthalene relative to 1 m³ of the oxygen-containing gas at standard temperature and pressure.

3. A process according to claim 1, wherein said catalyst further comprises niobium; phosphorus; antimony; and at least one member selected from the group consisting of sodium, potassium, rubidium, cesium, and thallium.

4. A process according to claim 1, wherein each catalyst packed in each individual catalytic layer is supported on an inert carrier, and said supported catalyst is packed in such a manner that the voidage of each individual catalytic layer sequentially decreases in the order from said first catalytic layer to subsequent catalytic layers.

5. A process according to claim 1, wherein each catalyst packed in each individual catalytic layer is supported on an inert carrier, and the supporting rate of said supported catalyst sequentially increases in the order from said first catalytic layer to subsequent catalytic layers.

6. A process according to claim 1, wherein each individual catalytic layer comprises a mixture of each catalyst and an inert substance, and the content of said inert substance in said mixture sequentially decreases in the order from said first catalytic layer to subsequent catalytic layers.

7. A process according to claim 3, wherein the phosphorus content of each catalyst for use in each individual catalytic layer sequentially increases in the order from said first catalytic layer to subsequent catalytic layers.

8. A process according to claim 3, wherein the total content of said sodium, potassium, cesium, rubidium, and thallium in each individual catalytic layer sequentially decreases in the order from said first catalytic layer to subsequent catalytic layers.

9. A process according to claim 8, wherein each catalyst packed in each individual catalytic layer is supported on an inert carrier, and said supported catalyst is packed in such a manner that the voidage of each individual catalytic layer sequentially decreases in the order from said first catalytic layer to subsequent catalytic layers.

10. A process according to claim 8, wherein each catalyst packed in each individual catalytic layer is supported on an inert carrier, and the supporting rate of said each catalyst sequentially increases in the order from said first catalytic layer to subsequent catalytic layers.

11. A process according to claim 1, wherein said each individual catalytic layer is held at a temperature of heat transfer medium sequentially increasing in the order from said first catalytic layer to subsequent catalytic layers.

12. A process according to claim 1, wherein a single reactor is used, and each individual catalytic layer is stacked in said reactor.

13. A process according to claim 1, wherein plural reactors are used, and catalytic layers formed in said individual reactors are connected to one another in such a manner that the conversion rate from ortho-xylene, or naphthalene, or both at an outlet of the first catalytic layer is 30% to 70%, and the conversion rate from ortho-xylene, or naphthalene, or both at an outlet of the second catalytic layer is 70% or more.

14. A process for producing phthalic anhydride through gas-phase catalytic oxidation of ortho-xylene, or naphthalene, or both with an oxygen-containing gas using one or more fixed bed reactors, wherein said gas-phase catalytic reaction is performed in three individual catalytic layers, wherein each catalyst for use in each individual catalytic layer comprises vanadium oxide and titanium oxide, the conversion rate from ortho-xylene, or naphthalene, or both at an outlet of a first catalytic layer is 30% to 70%, the conversion rate from ortho-xylene, or naphthalene, or both at an outlet of a second catalytic layer subsequent to said first catalytic layer is 70% to 95%, and the conversion rate from ortho-xylene, or naphthalene, or both at an outlet of a third catalytic layer subsequent to said second catalytic layer is 99% or more.

15. A process according to claim 14, wherein $\Delta T$ as defined according to the following equation is 0.35 to 0.85° C./(g/Nm$^3$) in the first catalytic layer, is 0.45 to 1.20° C./(g/Nm$^3$) in the second catalytic layer, and is 0.25 to 0.70° C./(g/Nm$^3$) in the third catalytic layer:

$$\Delta T = (HS - M)/W$$

wherein HS is the hot spot temperature (°C.) in each individual catalytic layer, M is the temperature (°C.) at which each individual catalytic layer is held, and W is the total amount (g) of ortho-xylene and naphthalene relative to 1 m$^3$ of the oxygen-containing gas at standard temperature and pressure.

* * * * *